United States Patent [19]

Reynolds

[11] Patent Number: 4,993,406
[45] Date of Patent: Feb. 19, 1991

[54] DEVICE FOR DAMPENING UNCONTROLLED MOVEMENT OF SURGICAL INSTRUMENTS

[76] Inventor: William V. Reynolds, 348 Rte. 32, Central Valley, N.Y. 10917

[21] Appl. No.: 407,822

[22] Filed: Sep. 14, 1989

[51] Int. Cl.⁵ ............................................. A61B 1/22
[52] U.S. Cl. ........................................ 128/9; 128/3; 128/10; 128/DIG. 26; 606/1
[58] Field of Search .......... 128/4, 9, 10, 11, DIG. 26; 606/106, 109, 162, 1; 269/1, 902, 909, 52

[56] References Cited

U.S. PATENT DOCUMENTS

| | | | |
|---|---|---|---|
| 3,020,912 | 2/1962 | Chester | 128/9 |
| 3,805,770 | 4/1974 | Okada | 128/4 |
| 4,360,025 | 11/1982 | Edwards | 128/DIG. 26 |
| 4,441,485 | 8/1984 | Reynolds | 128/9 |
| 4,717,385 | 1/1988 | Cameron et al. | 128/DIG. 26 |
| 4,897,081 | 1/1990 | Poirier et al. | 128/DIG. 26 |

*Primary Examiner*—Edward M. Coven
*Assistant Examiner*—Mark S. Graham
*Attorney, Agent, or Firm*—Millen, White & Zelano

[57] ABSTRACT

An inexpensive and disposable stabilizing support for surgical instruments is configured for use with a speculum, or the like. The support includes a spring-mounted bridge therein having a plurality of grooves in which a surgical instrument rests during microsurgery on a patient's ear, nose, or throat.

14 Claims, 3 Drawing Sheets

4,993,406

DEVICE FOR DAMPENING UNCONTROLLED MOVEMENT OF SURGICAL INSTRUMENTS

BACKGROUND OF THE INVENTION

1. Field of the Invention

This invention relates to devices for aiding surgeons while performing operations such as ear, nose, and throat operations, and more particularly to devices for dampening uncontrolled movement of surgical instruments.

2. Description of the Prior Art

Various devices are known for preventing damage to the ear during surgery. A device for preventing hazards during a myringotomy or a similar operations is described in U.S. Pat. No. 3,020,912. The device includes a battery-powered motor for providing rotary motion to a surgical knife through a set of drive gears. The operation of this device is complicated because of the motor drive and the gearing. Moreover, it is bulky because of the addition of a battery pack for powering the motor.

During ear surgery, the foregoing device is attached to an ear speculum at its wide funnel-shaped opening. The surgical knife extends therethrough and projects out of the tapered end of the speculum into the ear. The surgical knife is supported by a plurality of ball bearings to prevent wobble and friction. One of the plurality of bearings is mounted on the inner wall of the speculum. This bearing is semi-circular in shape and forms a cradle to support the rotating surgical blade and to prevent the blade from wobbling.

Although the motor-driven surgical knife is functional and prevents wobble, it is not cost effective because of the need for batteries, a motor, and associated gearings, bearings, and complicated attachments. Furthermore, the device is too expensive to be disposed of after each surgical use.

Shortcomings of devices such as that disclosed in U.S. Pat. No. 3,020,912 and growing recognition of the need to steady the surgeon's hand in such delicate operations as ear, nose, and throat surgery led to the instant inventor's creation of the coil spring device disclosed and claimed in U.S. Pat. No. 4,441,485. While the device of this prior patent functions adequately, there is considerable room for improvement in that the device presents significant manufacturing obstacles, as well as difficulties in use. There has yet to be devised a satisfactory, inexpensive method of securing the coil spring inside the speculum without having the ends of the spring protruding through the wall of the speculum and extending beyond the outer surface thereof. It is also somewhat difficult to properly insert the shank of the surgical instrument between the coils of the coil spring. These and other difficulties hindered widespread utilization of what is basically a very sound and useful concept.

OBJECTS OF THE INVENTION

It is an object of the present invention to provide a stabilizing support for surgical instruments that is simple in construction and is helpful in controlling the movements of a surgeon performing operations such as ear, nose, and throat operations.

It is another object of the present invention to provide a stabilizing support for surgical instruments that can be constructed from readily available, inexpensive materials.

A further object of the present invention is to provide a stabilizing support for surgical instruments that can be discarded after each use.

Upon further study of the specification and appended claims, further objects and advantages of this invention will become apparent to those skilled in the art.

SUMMARY OF THE INVENTION

The foregoing objects are accomplished through the use of a stabilizing support for surgical instruments for ear, nose, and throat operations that is designed to be both inexpensive and disposable after each use. The stabilizing support is used with a speculum for steadying the surgical instrument that rests thereon. The stabilizing support has a circular mounting flange which conforms to the diameter of the speculum and a spring-supported bridge having a plurality of grooves in which the shank of the surgical instrument rests. The surgical device may be used in combination with other surgical devices such as an otoscope or laryngoscope.

BRIEF DESCRIPTION OF THE DRAWINGS

The foregoing and other objects, features, and advantages of the invention will become apparent from the following in-depth description of a preferred embodiment thereof as illustrated in the accompanying drawings, in which like reference numerals designate the same or similar parts throughout the several views and wherein.

DESCRIPTION OF THE PREFERRED EMBODIMENT

Figure 1:
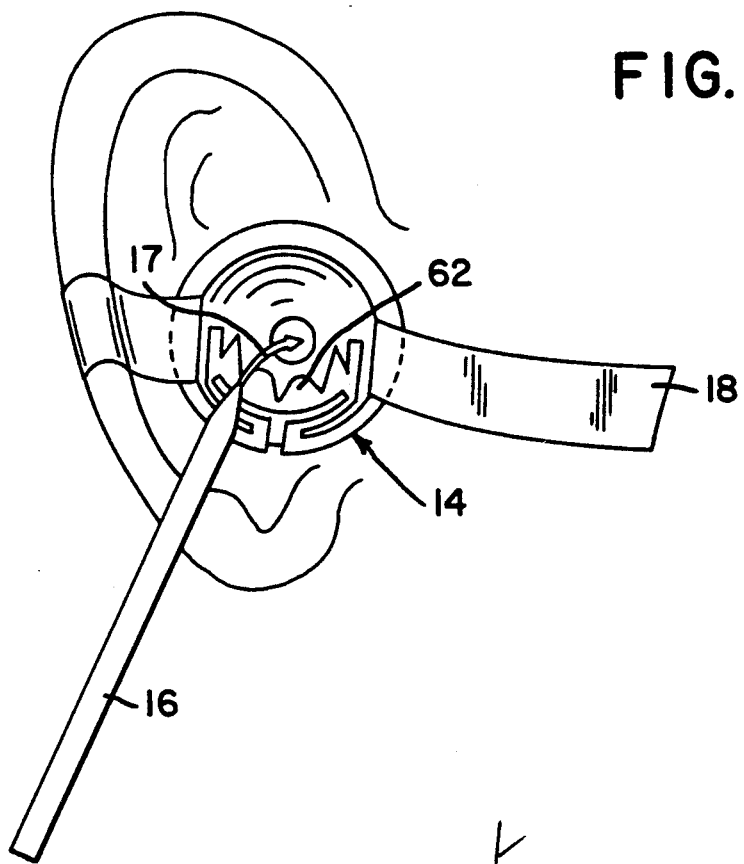
FIG. 1 is an enlarged elevation view of one embodiment of the stabilizing support of the present invention illustrating its use.
Figure 2:
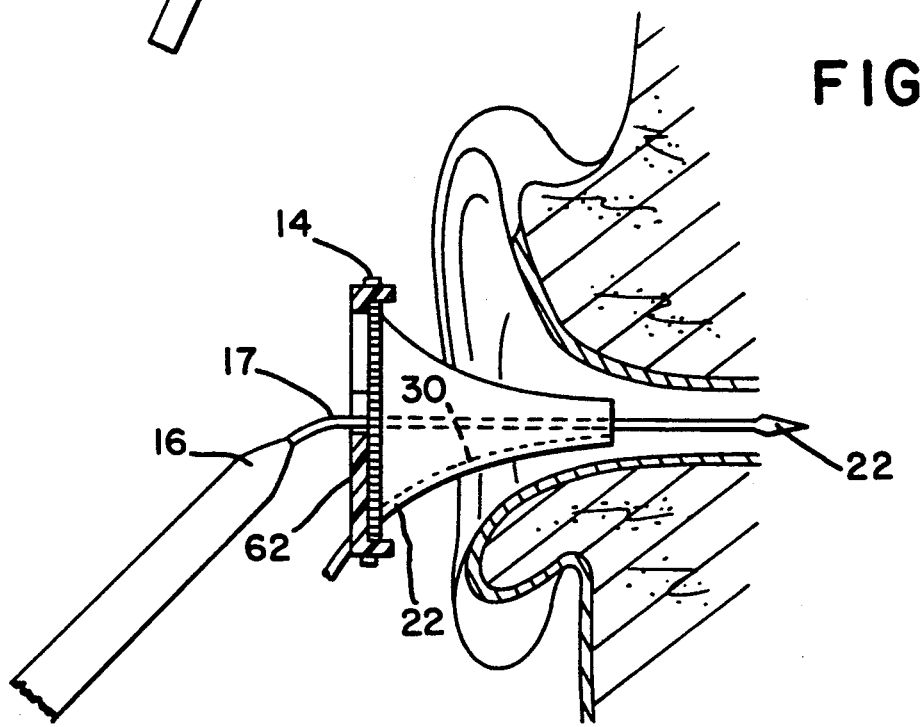
FIG. 2 is a side view in elevation of the stabilizing support of FIG. 1, with the human ear shown in cross-section.

Referring to FIGS. 1 and 2, there is shown a first embodiment of the invention comprising the combination of a speculum 12, a stabilizing support, generally designated by the numeral 14, a surgical instrument 16, and adhesive strips 18 for holding the speculum 12 in intimate contact with the ear 20, in which an operation is being performed.

The speculum 12 is designed particularly for ear surgery performed under magnification with an operating room microscope (not shown). The speculum has a conventional funnel shape, as seen more clearly in FIG. 2 is usually made of plastic but may be made of metal. The wider end 22 of the speculum 12 rests against the outer portion of the ear, whereas the tapered portion 24 of the speculum is inserted into the inner portion of the ear canal. As seen in FIG. 2, the cutting edge 26 of the surgical instrument 16 extends through the tapered portion 24 of the speculum into the ear canal adjacent the eardrum. Optionally, a suction tube 30 is secured to the inner surface 32 of the speculum 12 for removing blood and other fluids which may accumulate during surgery. The suction tube may be in the form of a tunnel embedded in the wall of the speculum 12.

Figure 3:
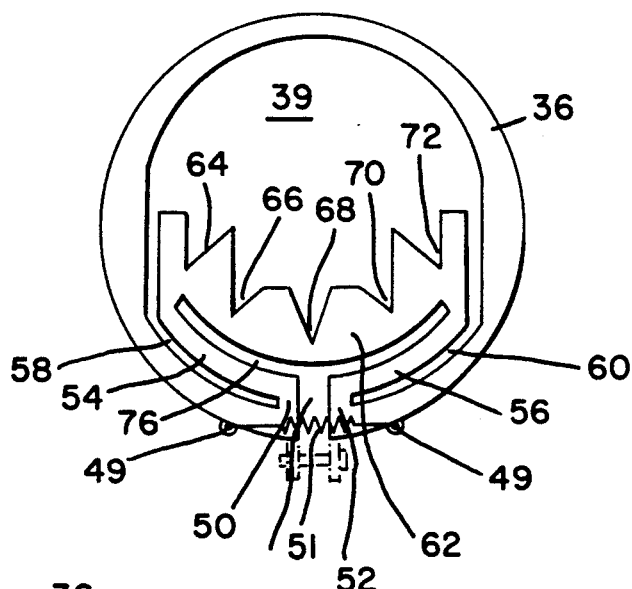
FIG. 3 is an enlarged planar view of a first embodiment of the stabilizing support of the instant invention shown detached from the speculum.
Figure 4:
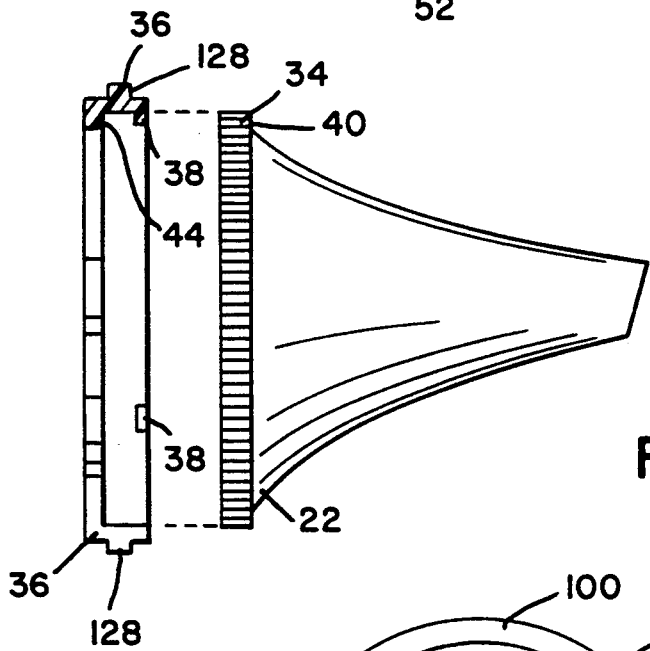
FIG. 4 is an enlarged side view of the stabilizing support of FIG. 3 in alignment with the speculum.

Referring now more specifically to FIGS. 3–4, where the stabilizing support is shown detached from the speculum 12, it is seen that the stabilizing support is a separate unit which may be secured to the wide end 22 of any conventionally dimensioned speculum. Generally, speculums have a peripheral rim 34 surrounding the wide end 22. The stabilizing support 14 of the instant invention has an axially extending peripheral flange 36, with a plurality of detents 38 extending inwardly therefrom which snap over the back side 40 of the peripheral rim 34. The front side 42 of the peripheral rim 34 abuts a shoulder 44 on the stabilizing support 14, which is spaced axially from the detents 38 and extends inwardly with respect to the peripheral flange 36 of the stabilizing support.

The peripheral flange 36 of the stabilizing support 14 is substantially circular defining an open area 39. A gap 48 is provided in the peripheral flange 36 to allow the peripheral flange to expand slightly and easily snap over the peripheral rim 34 of the speculum 12. Optionally, the peripheral flange can be provided with a pair of hooked projections 49, which retain a small coil spring 51 (or, optionally, an elastic band) that urges the gap 48 closed so that the stabilizing support is held securely on the speculum 12. Optionally, a pair of tabs 53 project from the peripheral flange 36, which tabs receive a screw 55 threaded into each one of the tabs so as to close the gap 48 when the screw advances.

Extending inwardly from the peripheral flange 36, adjacent the gap 48, are a pair of short struts 50 and 52 attached at first ends to the peripheral flange. A pair of oppositely extending, arcuately configured arms 54 and 56 are respectively attached at first ends thereof to second ends of the struts 50 and 52. The arms 54 and 56 are separated from the flange 36 by spaces 58 and 60. The ends of the arms 54 and 56 opposite the short struts 50 and 52 are joined by a rigid plate in the form of a bridge 62 having a plurality of grooves 64, 66, 68, 70, and 72, in which the shank 17 of the surgical instrument 16 rests during surgery (see FIGS. 1 and 2). The bridge 62 is relatively stiff in and of itself so as to provide a firm support for the shank 17 of the surgical instrument 16, but is spaced from the arms 54 and 56 by a gap 76 so as to provide the entire support structure with resiliency, which serves to dampen abrupt motions. The spaces 58 and 60 adjacent the arms 54 and 56 allow the rigid plate or bridge 62 to shift from side to side, bending one of the arms 54 or 56 toward the flange 36 and the other away from the flange. When pressure is placed on the center notch 68, the gap 76 and the gaps 58 and 60 allow the bridge 62 to deflect slightly in a downward direction, thus dampening abrupt movements.

Each of the grooves 64, 66, 68, 70, and 72 is generally V-shaped in configuration so as to guide the shank 17 of the surgical knife 16 smoothly to the bottom of the groove. Since the entire assembly including the grooves are made of plastic, the shank 17 slides readily in the axial direction against a slight frictional drag and does not bind in the grooves.

Figure 5:
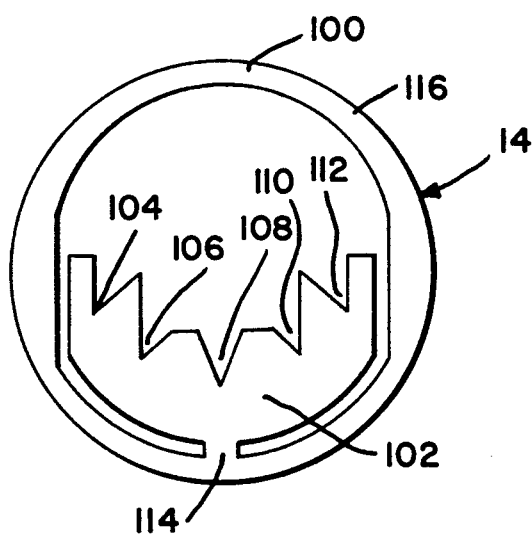
FIG. 5 is an enlarged planar view of a second embodiment of a stabilizing support configured in accordance with the instant invention.

Referring now to FIG. 5, there is shown a second embodiment of the stabilizing support spring in accordance with the instant invention, wherein the support spring has a peripheral flange 100 which is substantially identical to the peripheral flange 36 of FIGS. 1–6. However, the peripheral flange 100 does not have a gap such as the gap 48. The bridge 102 of the embodiment shown of the flange 100 in FIG. 5 has grooves 104, 106, 108, 110, and 112, substantially similar to the grooves 64, 66, 68, 70, and 72 of bridge 62 shown in FIG. 3. However, the bridge 102 of FIG. 5 is mounted on a single, resilient support post 114, which allows the bridge 102 to rock slightly against the resistance of the support post 114 so as to dampen forces exerted by the shank 17 of the surgical instrument 16 (see FIG. 2).

As stated previously, the foregoing surgical unit is especially useful for ear surgery. More specifically, the speculum 12 and stabilizing support 14 are ideally suited for operating on the eardrum, middle ear, or sheath of the facial nerve or inner ear.

During surgery on the ear, the speculum 12 and the stabilizing support 14 are held stationary with respect to ear by adhesive strips 18. With the aid of a microscope (not shown), surgery can be performed. The stabilizing support 14 dampens unintentional movements of the operating surgeon, minimizing the likelihood of injury caused by unintentional movement of the surgical instrument 16. For while example, sudden inward or lateral movements of the surgical instrument 16 are impeded by drag against the walls of the grooves, voluntary movements made by the operating surgeon are enhanced due to control provided by the grooves.

Figure 6A:
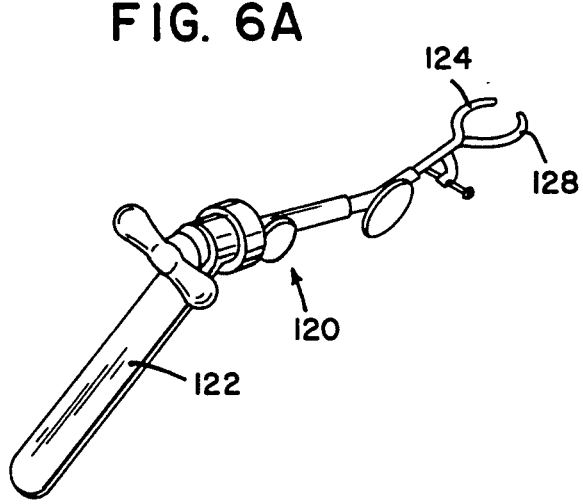
FIG. 6A is a perspective view of a stabilizing support configured in accordance with the instant invention and used with a speculum holder which can be clamped to an operating table.
Figure 6B:
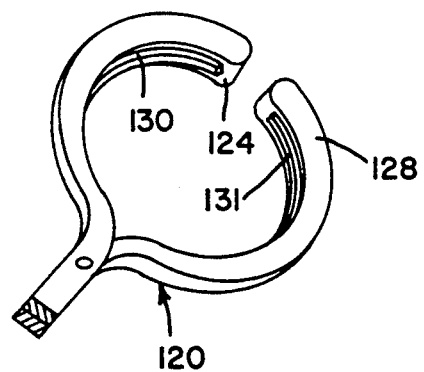
FIG. 6B shows grooved jaws for receiving a speculum equipped with a stabilizing support configured in accordance with the instant invention.

Referring now to FIG. 6, there is shown a speculum holder, designated generally by the numeral 120, which can be clamped to an operating table by a sliding bar 122. The speculum holder includes a pair of opposed jaws 124 and 126 for holding a speculum such as the speculum 12 shown in FIGS. 1 and 2. In order to retain the speculum 12 between the jaws 124 and 126 when the speculum is used with the stabilizing support such as the support 14, the peripheral flange 36 has a peripheral rib 128 formed on the flange 36, which rib is received in slots 130 and 131 in the jaws 124 and 126.

Figure 7:
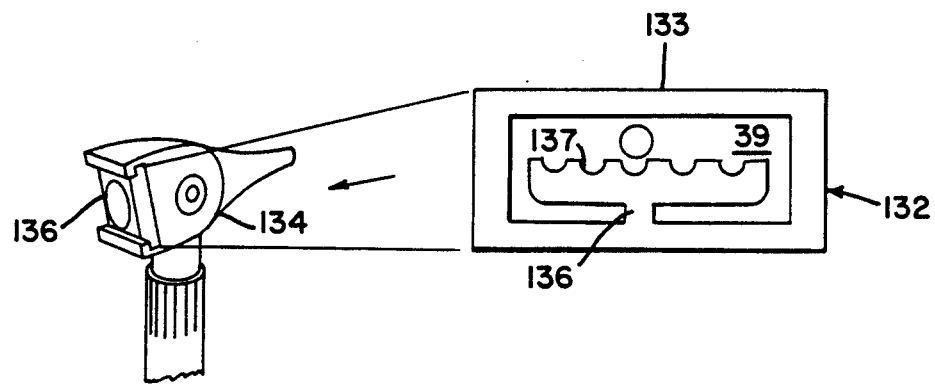
FIG. 7 illustrates utilization of the stabilizing support of the instant invention with an otoscope.

Referring now to FIG. 7, there is shown a third embodiment of the invention wherein a stabilizing support 132 is configured with a rectangular frame 133 for use with an otoscope 134. The stabilizing support 132 is mounted on the otoscope 134 beside the lens 136 of the otoscope. Preferably, the bridge 137 of the rectangular stabilizing support 132 is supported by a post 136, which is similar to the post 114 of FIG. 5.

Figure 8:
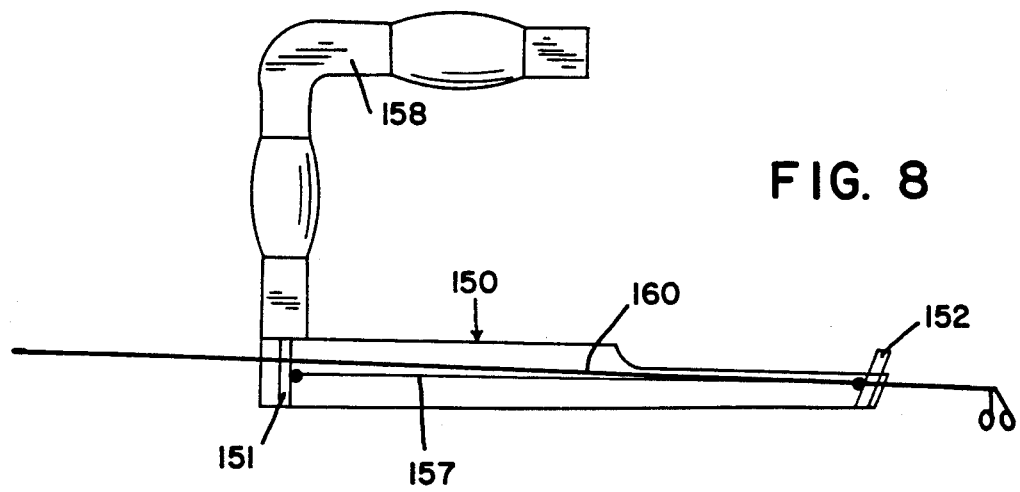
FIG. 8 illustrates utilization of a stabilizing support of the instant invention with a laryngoscope.

Referring now to FIG. 8, a laryngoscope, designated generally by the numeral 150, is shown with a pair of stabilizing supports 151 and 152, similar in configuration to the stabilizing support 14 of FIGS. 35, which are positioned at the inner end 155 and outer end 156 of the laryngoscope. The stabilizing supports 151 and 152 are held in place by an elastic band 157 positioned outside of the laryngoscope attached thereto and extending therebetween. The laryngoscope 150 is manipulated by a handle 158, while a surgical or other instrument 160 rests in the grooves of the stabilizing supports 151 and 152.

Other microsurgical applications for the surgical unit are possible (e.g., eye surgery, suturing of tendons, nerve sheaths, and paranasal sinuses, etc.). The invention may also be used in industry for assembling minute structures in, e.g., computer components, hearing aids, or watches. Consequently, the features of the apparatus may be changed or varied without departing from the essence of the invention defined in the following claims.

What is claimed is:

1. A stabilizing support for a surgical instrument used with a speculum, wherein the speculum has a wall with an inner surface formed about an axis for guiding the instrument, the stabilizing support comprising:
a peripheral flange adapted to be mounted on the speculum, the peripheral flange enclosing an open area;
a relative rigid plate disposed in the open area, the relatively rigid plate having between ends thereof a plurality of grooves therein opening toward the axis of the support in which grooves the surgical instrument is adapted to rest; and
resilient support means connecting the rigid plate to the peripheral flange wherein the surgical instrument is stabilized due to damping of the unintentional forces imparted to the instrument by the surgeon.

2. The stabilizing support of claim 1, wherein the resilient support means comprises a single post supporting the relatively rigid plate intermediate the ends of the plate.

3. The stabilizing support of claim 1, wherein the resilient support means comprises a pair of spaced struts, each having first and second ends and each attached at the first end to the peripheral flange and extending into the open area, and a pair of oppositely directed arms having first and second ends and attached at one end to the second ends of the struts in spaced relation to the peripheral flange, the relatively rigid plate being attached to the second ends of the arms and bridging the arms in spaced relation thereto.

4. The stabilizing support of claim 3, wherein the struts project from the flange adjacent a gap in the flange, which gap allows the flange to flex slightly so as to be adapted to fit over and snap behind a peripheral rim on the speculum.

5. The stabilizing support of claim 4, wherein the peripheral flange thereof includes a shoulder adapted for abutment with the front of the speculum and a plurality of projecting detents in spaced relation to the shoulder adapted for engaging behind the peripheral rim of the speculum.

6. The stabilizing support of claim 5, further including elastic means for urging the flange to close the gap so as to be adapted to secure the flange on the speculum.

7. The stabilizing support of claim 6, wherein the means for urging the gap closed is an elastic connected sides of the gap.

8. The stabilizing support of claim 6, wherein the means for urging the gap closed includes a screw attached to the flange which spans the gap and closes the gap upon advancing.

9. The stabilizing support of claim 1, wherein the flange includes a hole therethrough to receive therethrough a suction tube adapted to extend in juxtaposition with the wall of the speculum.

10. The stabilizing support of claim 1, wherein the peripheral flange is rectangular for cooperation with an otoscope.

11. The stabilizing support of claim 1, wherein the peripheral flange includes a projecting rib for receipt in a groove in the jaws of an operating table mounting clamp.

12. In combination, a laryngoscope formed about a central axis and a pair of stabilizing supports mounted at opposite ends of the laryngoscope in coaxial relation therewith, the combination adapted to support a surgical instrument thereon, wherein each stabilizing support comprises:
a peripheral flange for mounting the stabilizing support on the laryngoscope, the peripheral flange being in spaced relation to the central axis, the peripheral flange enclosing an open area;
a relatively rigid plate disposed in the open area, the relatively rigid plate having a plurality of grooves therein opening toward the axis of the laryngoscope in which grooves the surgical instrument is adapted to rest; and
resilient support means connecting the rigid plate to the peripheral flange wherein the surgical instrument may be stabilized due to damping of the unintentional forces imparted to the instrument by the surgeon.

13. The stabilizing support of claim 6, wherein the elastic means is a coil spring.

14. The stabilizing support of claim 1, wherein the flange includes a recess therein adapted to accommodate a tunnel formed in the speculum wall.

* * * * *